(12) United States Patent
Li et al.

(10) Patent No.: US 6,830,834 B2
(45) Date of Patent: Dec. 14, 2004

(54) ORGANIC LIGHT EMITTING DEVICES WITH HOST-GUEST BONDING

(75) Inventors: Xiao-Chang Charles Li, Union City, CA (US); Jian Ping Chen, Palo Alto, CA (US); Kazunori Ueno, Ebina (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/424,972

(22) Filed: Apr. 29, 2003

(65) Prior Publication Data

US 2004/0219387 A1 Nov. 4, 2004

(51) Int. Cl.$^7$ ............... H05B 33/12; H05B 33/14; C08G 79/02; C09K 11/06
(52) U.S. Cl. ............... 428/690; 428/917; 313/504; 313/506; 257/102; 257/103; 252/301.16; 564/308; 528/398
(58) Field of Search ............... 428/690, 917; 313/504, 506; 257/102, 103; 252/301.16; 564/308; 528/398

(56) References Cited

U.S. PATENT DOCUMENTS

| | | | |
|---|---|---|---|
| 3,409,594 A | 11/1968 | Slovinsky | 260/67 |
| 4,127,412 A | 11/1978 | Rule | 96/1 PC |
| 4,547,317 A | 10/1985 | Kamhi | 252/700 |
| 4,614,609 A | 9/1986 | Inoue | 252/299.66 |
| 4,668,427 A | 5/1987 | Saito | 252/299.66 |
| 4,676,925 A | 6/1987 | Inoue | 252/299.65 |
| 4,751,019 A | 6/1988 | Saito | 252/299.66 |
| 5,121,029 A | 6/1992 | Hosokawa et al. | 313/504 |
| 5,225,508 A | 7/1993 | Tamura et al. | 526/289 |
| 5,354,511 A | 10/1994 | Wu et al. | 252/582 |
| 5,700,393 A | 12/1997 | Kelly | 252/299.63 |
| 5,709,720 A | 1/1998 | Cherpack | 44/413 |
| 5,834,621 A | 11/1998 | Yamamoto et al. | 560/221 |
| 6,040,462 A | 3/2000 | Oh et al. | 549/352 |
| 6,303,238 B1 | 10/2001 | Thompson et al. | 428/690 |

FOREIGN PATENT DOCUMENTS

| | | |
|---|---|---|
| EP | 0 281 381 | 7/1992 |
| JP | 2001-11926511 | 7/2001 |

OTHER PUBLICATIONS

W.S. Wadsworth, Jr., W.D. Emmons, "The Utility of Phosphonate Carbanions in Olefin Synthesis", *J. Am. Chem. Soc.*, vol. 83, 1733 (1961).

*Primary Examiner*—Dawn Garrett
(74) *Attorney, Agent, or Firm*—Fitzpatrick, Cella, Harper and Scinto

(57) ABSTRACT

A compound having a host moiety chemically bonded to at least one guest moiety according to the following general molecular structure:

$$H_o-(L-G)_n.$$

$H_o$ represents a host moiety that receives hole and/or electron recombination energy and transfers that energy to a guest moiety; G represents a guest moiety that contains a luminescent chromophore; L represents a chemical moiety that links the host and guest moiety and n is from 1 to 4. The compound can be used in the emissive layer of an OLED, or as a dopant dispersed in a host material that forms the emissive layer, wherein the host material has the same chemical structure as $H_o$.

2 Claims, 4 Drawing Sheets

ORGANIC LIGHT EMITTING DEVICES WITH HOST-GUEST BONDING

BACKGROUND OF THE INVENTION

1. Field of the Invention

The present invention relates to compounds made by chemically bonding a host material with a guest material. These compounds are useful in an emissive layer of an organic light emitting device.

2. Description of the Related Art

Organic light emitting devices (OLEDs) typically comprise a layer of emissive material between an anode and a cathode. When a bias is applied across the electrodes, positive charges (holes) and negative charges (electrons) are respectively injected from the anode and cathode into the emissive layer. The holes and the electrons form excitons in the emissive layer to emit light.

Electrodes are chosen to facilitate charge injection. A transparent indium-tin-oxide (ITO) anode has a relatively high work function and is therefore suitable for use as a hole injection electrode, while low work function metals such as Al, Mg and Ca are suitable for injection of electrons.

To improve the power efficiency of an OLED, it is frequently desirable to enhance charge injection at the electrode interface. Hole transport layers and electron transport layers may be added adjacent the respective electrodes to facilitate charge transfer. Depending upon whether hole transport or electron transport is favored, the light emissive layer may be located closer to the anode or the cathode. In some instances, the emissive layer is located within the hole transport or electron transport layer.

Improved performance can be obtained if blocking layers are provided to block against the injection of either holes or electrons from the adjoining layer and their subsequent escape from the device. Likewise, a modifying layer may be used to improve the contact with one or both of the electrodes, or to improve the interface between two other layers.

Some of these layers can be combined. For example, a double-layered structure is fabricated from a combined hole-injecting and transporting layer together with a combined electron-transporting and light-emitting layer. Likewise, a triple-layered structure is composed of a hole-injecting and transporting layer, a light-emitting layer, and an electron-injecting and transporting layer.

Hole transport layers may include triarylamine-based materials, although many other hole transport materials are known. Likewise, an aluminum quinolinolate complex known as $AlQ_3$ is a well known electron-transport material which has been used in OLEDs, although other electron transport materials are known.

Emissive materials having widely varied structures are known in the art and are generally selected based on color, brightness, efficiency and lifetime. These emissive materials may themselves also have electron transport or hole transport characteristics.

In addition, it is possible to form these layers from a "host" material doped with another material (the "guest" material) designed to achieve the desired effect of the layer (for example, to achieve a hole transport effect, an electron transport effect, or an emissive effect). One conventional method of dispersing the guest molecules into the host is coevaporation. In the case of an emissive guest-host system, the host must be able to transfer energy to the guest so that a maximum amount of energy contributes to emission by the guest rather than being absorbed by the host.

OLEDs have been produced that have more than one emissive layer. By using two or more emitter layers with different emission colors and adjusting the thickness of each emitter layer, the EL spectrum of the devices could be tuned to a desired color.

Occasionally, conventional methods of creating emissive layers do not yield a uniform dispersal of the guest throughout the host layer. Thus, in these emissive layers, the guest molecules may aggregate resulting in areas of the emissive layers being brighter than other areas.

Over time, as conventional emissive layers are used, they may exhibit guest molecule drifting. This also causes emissive layers to be nonuniform, resulting in uneven performance by different areas of the layer.

There continues to be a need for OLED materials exhibiting thermal stability, having bright, high purity luminescent emission, and for materials which contribute to greater luminescence per injected charge. There is particularly a need for OLED materials which solve the foregoing problems.

SUMMARY OF THE INVENTION

In an aspect of the present invention, a compound contains a host moiety chemically bonded to at least one guest moiety according to the following general molecular structure:

$$H_o\text{—}(L\text{—}G)_n.$$

$H_o$ represents a host moiety that receives hole, electron or hole and electron recombination energy and transfers that energy to the guest moiety. G represents a guest moiety that is a photoluminescent chromophore. L represents a direct bond or a chemical moiety that links the host and guest moiety. One to four guest moieties can be bonded to the host moiety.

Suitable hosts can be, but are not limited to, substituted or unsubstituted aromatic aryl groups, heteroaryl groups, polycyclic fused groups or combinations thereof linked by single bonds, double bonds, triple bonds or heteroatoms. Preferably, the host moiety is substituted or unsubstituted biphenyl, substituted or unsubstituted binaphthalyl, substituted or unsubstituted fluorenyl, substituted or unsubstituted pyrenyl or dimers, trimers or tetramers of fluorene, binaphthalene or pyrene.

The host moiety may contain a conjugated chromophore and moieties that have hole transport, electron transport or hole and electron transport capabilities. An example of a suitable host is three pyrenyl groups each linked to a bis-spiro-indanyl group by an oxygen atom.

Preferred guest moieties are conjugated chromophores containing at least one nitrogen that have a polarized property and a dipole moment. Guest moieties may have an aromatic ring, a heteroaromatic ring, a double bond, a triple bond or a combination thereof. Examples of suitable guest moieties are stilbenyl groups, fluorenyl groups and nitrogen containing ligands chelated with transition metals, rare earth metals or lanthanide metals. These guest moieties may have substituted groups such as arylamines or carbazolyls.

The host moieties and guest moieties can be bonded directly together or preferably have another moiety connecting them. The moiety connecting the host and guest moieties can have, but is not limited to, carbon, silicon, oxygen, sulfur, selenium, nitrogen or phosphorus or a combination thereof.

In some cases, the connecting moiety serves to interrupt conjugation between the most moiety and the guest moiety. One way to achieve this function is to have a connecting moiety that is not conjugated.

In another preferred embodiment, the connecting moiety is 5 to 100Å in length. More preferably, the connecting moiety is 10 to 50Å in length.

In another aspect of present invention, a compound is made of a host moiety chemically bonded to at least one guest moiety according to the following general molecular structure:

$$H_o-(X-(R)_m-X-G)_n$$

wherein $H_o$ represents a host moiety that receives hole and/or electron recombination energy and transfers that energy to the guest moiety; G represents a guest moiety that is a photoluminescent chromophore; X represents O, S, $CH_2$, $SO_2$, or Si or a combination thereof; R represents an alkyly group, a polycyclic group, a fused polycyclic group, an aromatic group or a fused aromatic group or a combination thereof; n is a number from one to four and m is a number from 0 to 20.

Another aspect of the present invention is organic light emitting devices containing the compounds described above. In the organic light emitting device, the compounds can serve as a dopant within a host layer or can constitute an emissive layer of their own.

In a preferred embodiment of the present invention, the compound is a dopant in a host layer wherein the host layer is substantially made of a compound which has substantially the same chemical structure as the dopant's host moiety. For example, when a compound of the formula $H_o-(L-G)$, is used as a dopant, the host layer is preferred to comprise a material which has substantially the same chemical structure as $H_o$.

The organic light emitting devices of the present invention in addition to the host-guest layer described above, may also have hole transporting layers, electron transporting layers, or both hole and electron transporting layers.

This brief summary has been provided so that the nature of the invention may be understood quickly. A more complete understanding of the invention can be obtained by reference to the following detailed description of the preferred embodiments thereof.

DETAILED DESCRIPTION OF THE PREFERRED EMBODIMENTS

Figure 1:
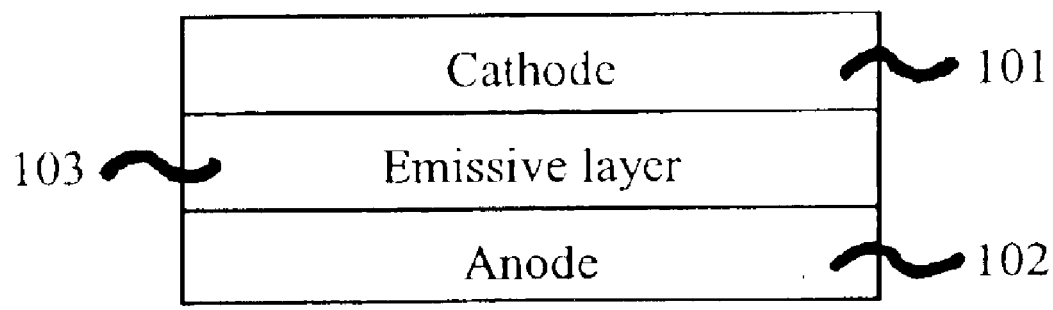
FIGS. 1 to 4 are schematic cross sectional views of OLEDs according to the invention.

The present invention provides a material for use in the emissive layer of an organic light emitting device (OLED) which provides some of the benefits of conventional host-dopant layers while avoiding some of the problems associated with the conventional systems. The present invention provides improved guest material dispersal in the host matrix, diminished guest material drift due to device operation, improved thermal stability and improved efficiency in host-guest interaction.

The present invention provides these advantages by providing compounds of the following general formula for use in an organic light emitting device:

$$H_o-(L-Q)_n.$$

In the above formula, $H_o$ represents a host moiety that receives hole, electron or hole and electron recombination energy and transfers that energy to the guest moiety. G represents a guest moiety that is a photoluminescent chromophore. L represents a direct bond or a chemical moiety that links the host and guest moiety. Up to four guest moieties can be bonded to the host moiety.

$H_o$ functions in an emissive layer as a host moiety which receives excitation energy and transfers that energy to the guest moiety by way of an emission or absorption energy transfer process. Preferably, the host moiety contains a conjugated chromophore and moieties that have hole transport, electron transport or hole and electron transport capabilities. Three pyrenyl groups each linked to a bis-spiro-indanyl group by an oxygen atom is an example of a suitable host moiety. Another example of a suitable host moiety is two phanthrenyl groups linked to a phenyl group.

Suitable host moieties can be, but are not limited to, substituted or unsubstituted aromatic aryl groups, heteroaryl groups, polycyciic fused groups or combinations thereof linked by single bonds, double bonds, triple bonds or heteroatoms. Preferably, the host moiety is substituted or unsubstituted biphenyl, substituted or unsubstituted binaphthalyl, substituted or unsubstituted fluorenyl, substituted or unsubstituted pyrenyl or dimers, trimers or tetramers of fluorene, binaphthalene or pyrene.

Preferably, the guest moieties (G) are conjugated chromophores containing at least one nitrogen that have a polarized property and a dipole moment. Guest moieties should have an aromatic ring, a heteroaromatic ring, a double bond, a triple bond or a combination thereof. Examples of suitable guest moieties are stilbenyl groups, fluorenyl groups and nitrogen containing ligands chelated with transition metals, rare earth metals or lanthanide metals. These guest moieties can have substitutent groups such as arylamines or carbazolyl.

In the present invention, L represents the bond between the host and the guest moiety. This can be a direct bond or preferably is a linking moiety. This linking moiety is made of carbon, silicon, oxygen, sulfur, selenium, nitrogen or phosphorus or a combination thereof.

In a preferred embodiment, the linking moiety serves as a conjugation breakage point between the host and guest moieties. Thus, conjugation between the host and guest moieties is interrupted and the host and guest moieties have separate conjugation systems. Thus, it is preferred that the linking moiety is not conjugated.

The linking moieties can vary in length, however, it is preferred that they are 5 to 100Å in length. More preferably, the linking moieties are 10 to 50Å in length. The length of the linking moiety and, therefore, the distance between the guest and the host moieties affects the efficiency of the electronic interaction between the host and the guest moiety. Consequently, manipulating the length of the linking moiety is one mechanism for enhancing the efficiency of the electronic interaction.

Another aspect of the present invention that provides the advantages discussed above is a compound made of a host moiety chemically bonded to at least one guest moiety according to the following general molecular structure:

$$H_o-(X-(R)_m-X-G)_n$$

wherein $H_o$ represents a host moiety that receives hole and/or electron recombination energy and transfers that energy to the guest moiety; G represents a guest moiety that is a photoluminescent chromophore; X represents O, S, $CH_2$, $SO_2$, or Si or a combination thereof; R represents an alkyly group, a polycyclic group, a fused polycyclic group, an aromatic group or a fused aromatic group or a combination thereof; n is a number from one to four and m is a number from 0 to 20. Suitable materials are provided above.

FIGS. 1 to 4 illustrate another aspect of the present invention. These figures show a schematic cross section of organic light emitting devices containing the compounds described above. FIG. 1 illustrates an OLED containing a cathode 101, an anode 102 and an emissive layer 103 comprising a compound of the present invention.

Figure 2:
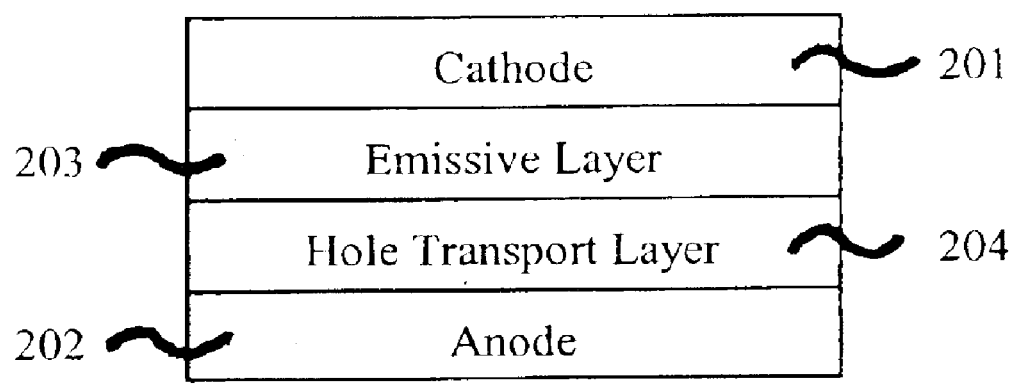
Figure 3:
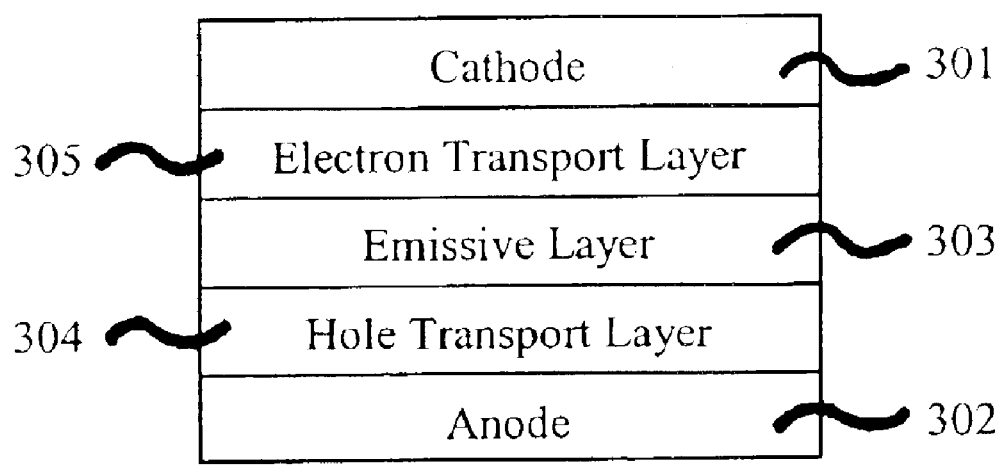

FIG. 2 is a view of an OLED containing a cathode 201, an anode 202, an emissive layer 203 containing a compound of the present invention, and a hole transporting layer 204. FIG. 3 shows a similar OLED containing an anode 302, cathode 301, emissive layer 303 and hole transport layer 304, with the addition of an electron transport layer 305.

Figure 4:
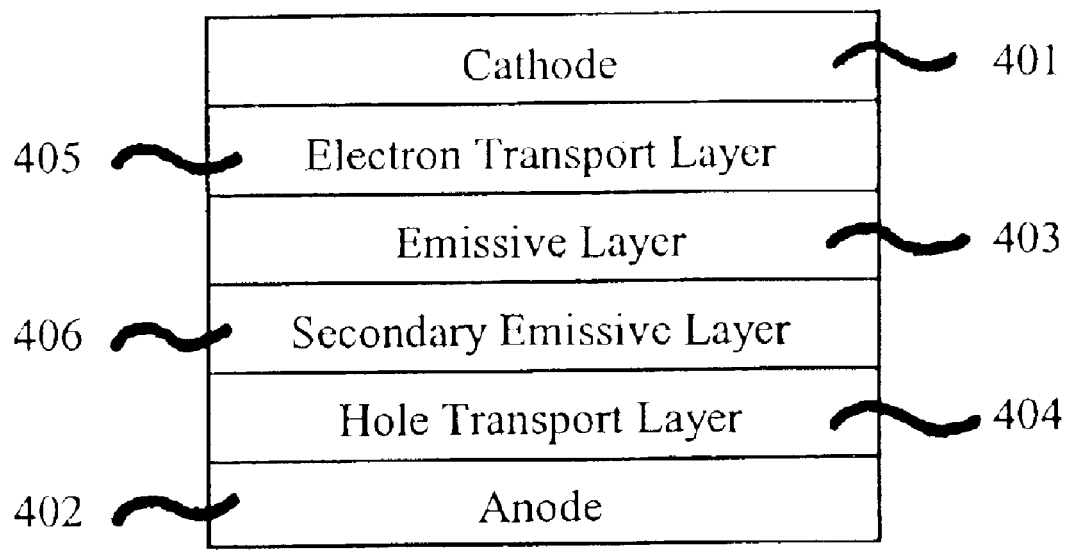

FIG. 4 is a schematic cross section of a multi-layer OLED containing two emissive layers. Using two or more emissive layers in one device allows for the emission of a color not normally produced by the emissive materials employed in the device. For example, a multi-layer OLED containing two emissive layers, one blue layer and one yellow layer, can produce white light.

In FIG. 4, emissive layer 403 is made of a host compound doped with a compound emitting either yellow or blue light. Secondary emissive layer 406 is made purely of the compound of the present invention and, therefore, layer 406 is free of a host compound. The OLED also contains a cathode 401, and anode 402, a hole transporting layer 404, and an electron transporting layer 405. As illustrated in FIG. 4, the compound of the present invention, in its pure form, can constitute an emissive layer. Therefore, the compound of the present invention can be used as a dopant or as the sole component of an emissive layer.

It is preferred, however, that the compound of the present invention is used as a dopant deposited in a host material. In a more preferred embodiment, the compound of the present invention is deposited in a host layer, wherein the host layer is made of a compound that has substantially the same chemical structure as the host moiety. Thus, it is preferable that when $H_o$ is a pyrenyl group, the host layer is made of pyrene or a compound with a substantially similar chemical structure.

OLEDs of the present invention can be fabricated by the following general procedure. First, a clean substrate is patterned with an ITO layer. Then, the substrate is treated with $O_2$ plasma for 1 to 5 minutes. Once treated, the substrate is placed in a thermal evaporator and the pressure is pumped down below $6 \times 10^{-6}$ torr. A host layer, with a the compound of the present invention serving as a dopant, is then evaporated onto the substrate. Optionally, a hole transport layer and/or an electron transport layer are also evaporated onto the substrate. Finally, another electrode layer is deposited thereon.

A preferred hole transporting material is 1,4-bis[(1-naphthyphenyl)-amino]biphenyl (NPD) and has the following structure:

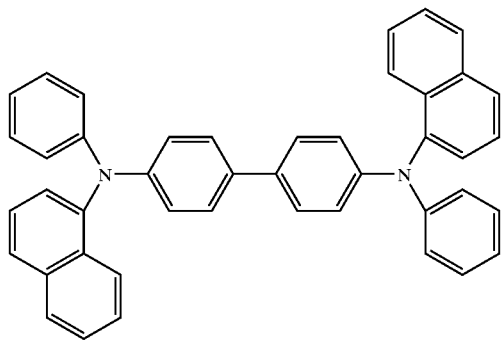

1,4-bis[(1-naphthyphenyl)-amino]biphenyl (NPD)

A preferred electron transport material is 4,7-diphenyl-1, 10-phenanthroline (Bphen) and has the following structure:

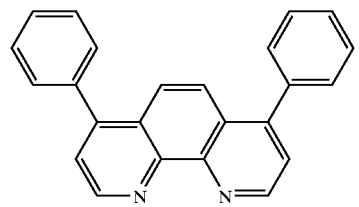

4,7-diphenyl-1,10-phenanthroline (Bphen)

Another suitable electron transport material which may be used in the present invention is aluminum tris(8-hydroxyquinoline) ($AlQ_3$) having the following structure:

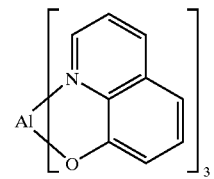

$AlQ_3$ (aluminum tris(8-hydroxyquinoline))

EXAMPLES

The following are compounds that are encompassed by the present invention.

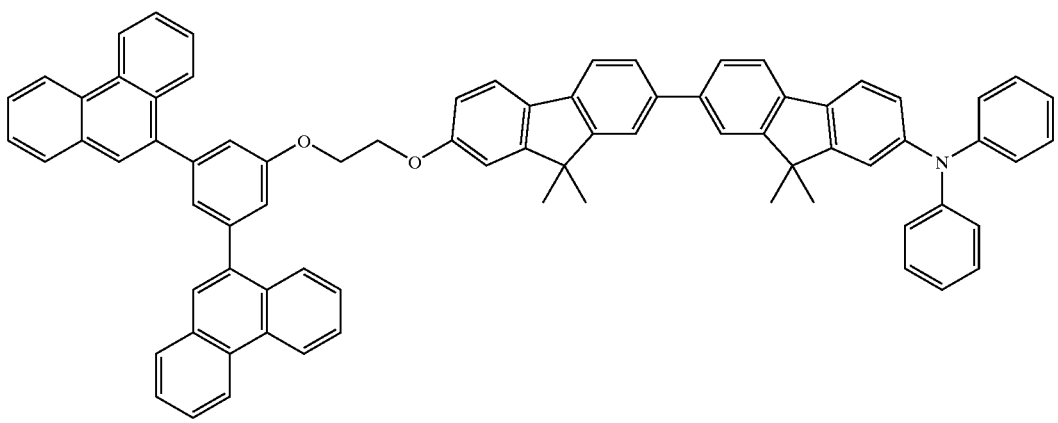

(i)

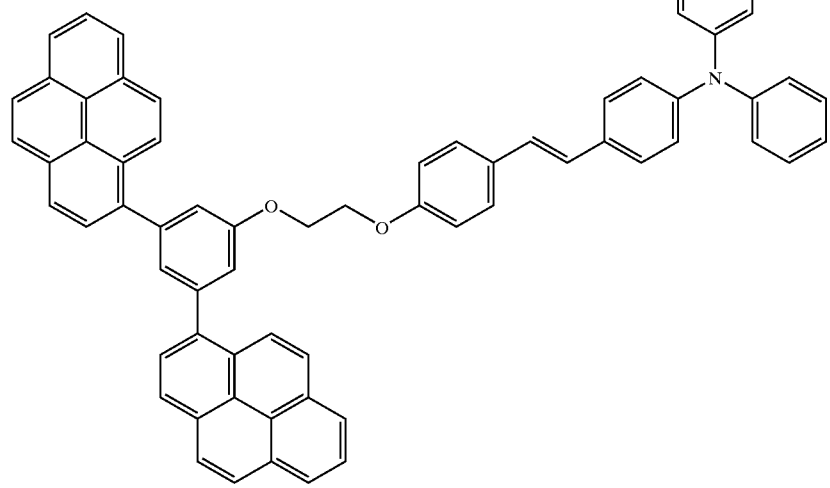
(ii)
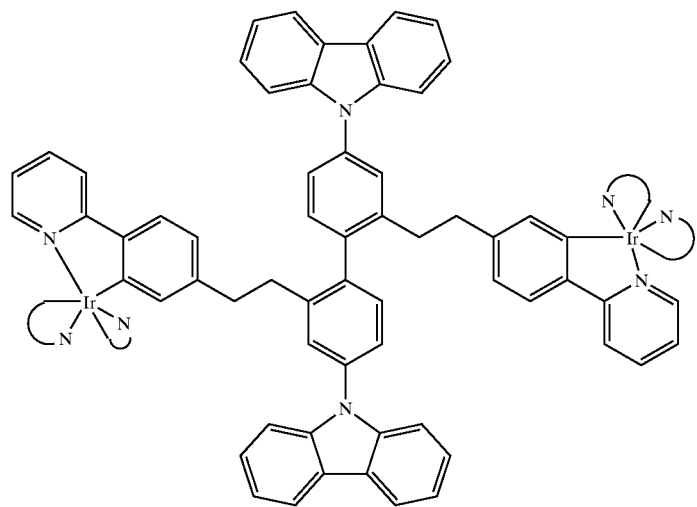
(iii)
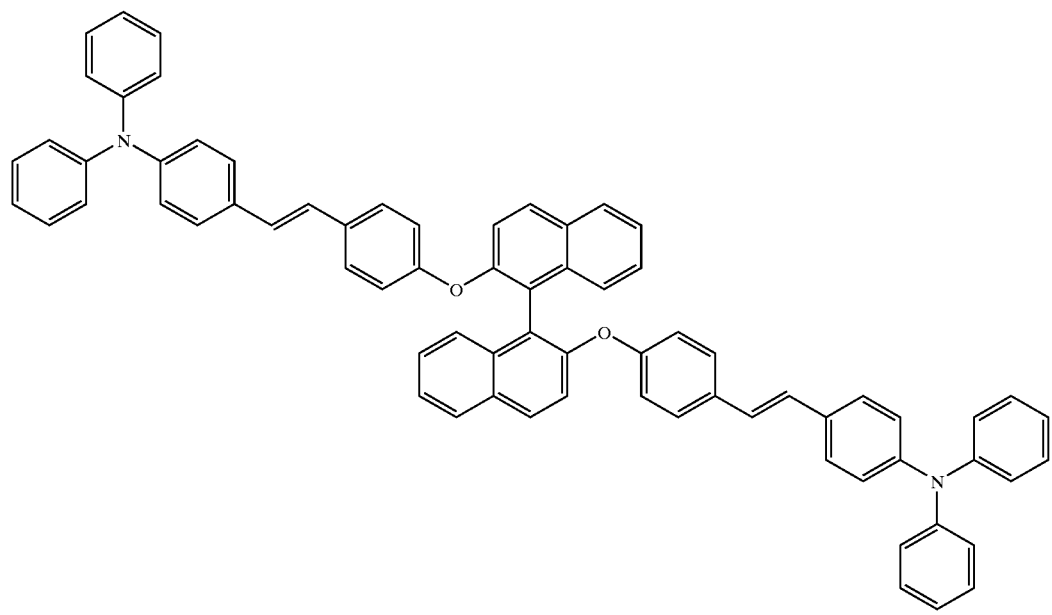
(iv)

-continued
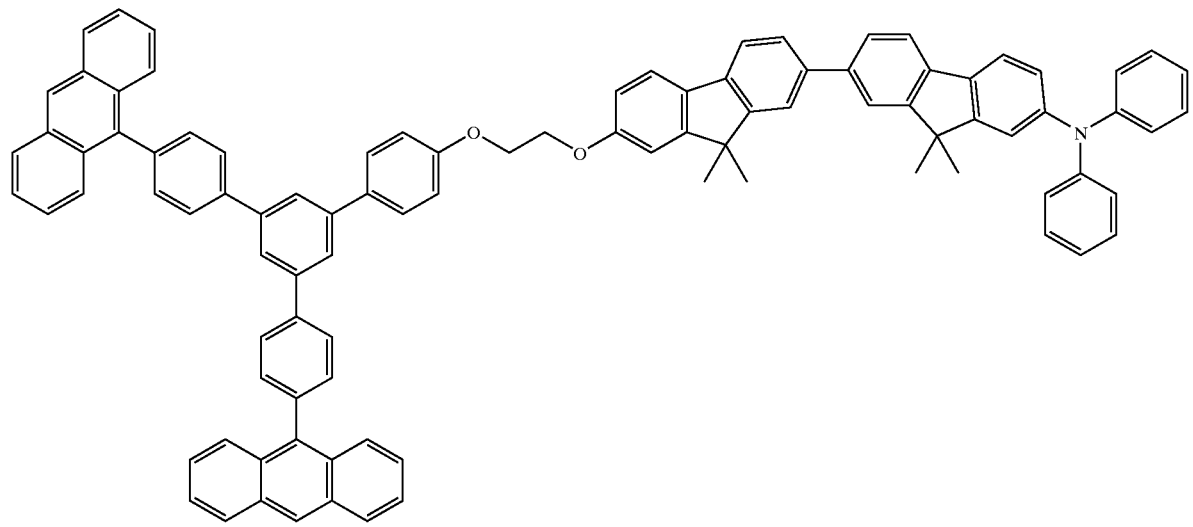
(v)
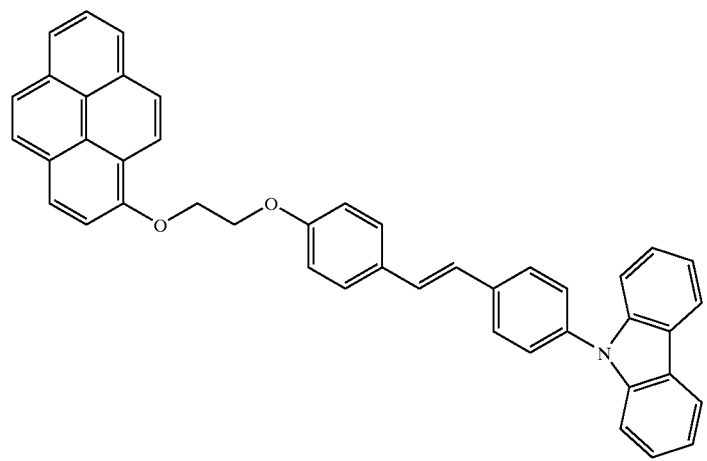
(vi)
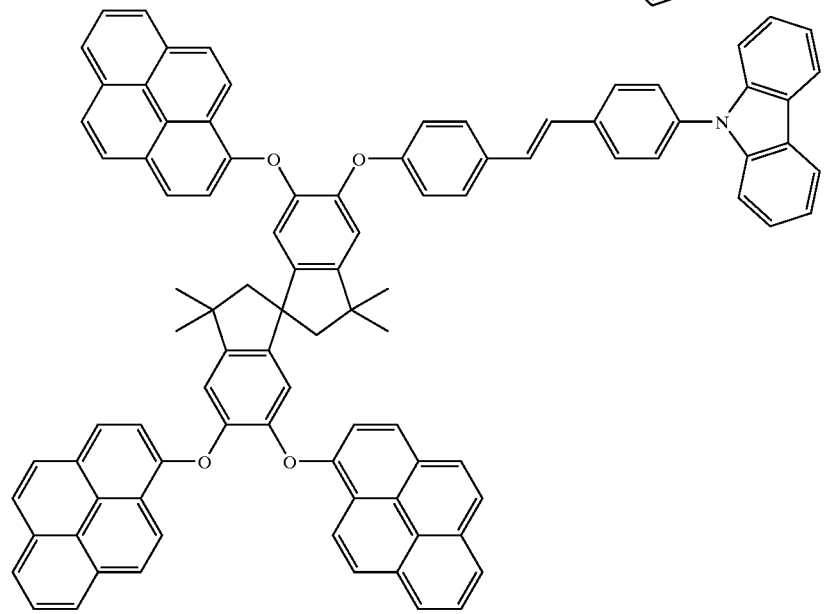
(vii)

-continued

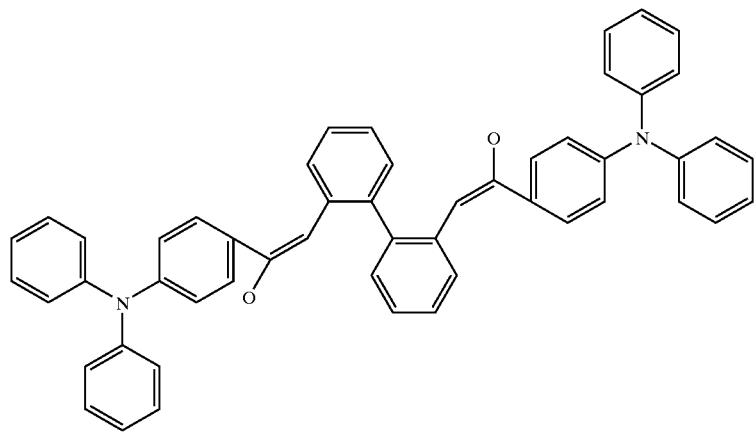

(viii)

Compound (viii) may be synthesized as follows:

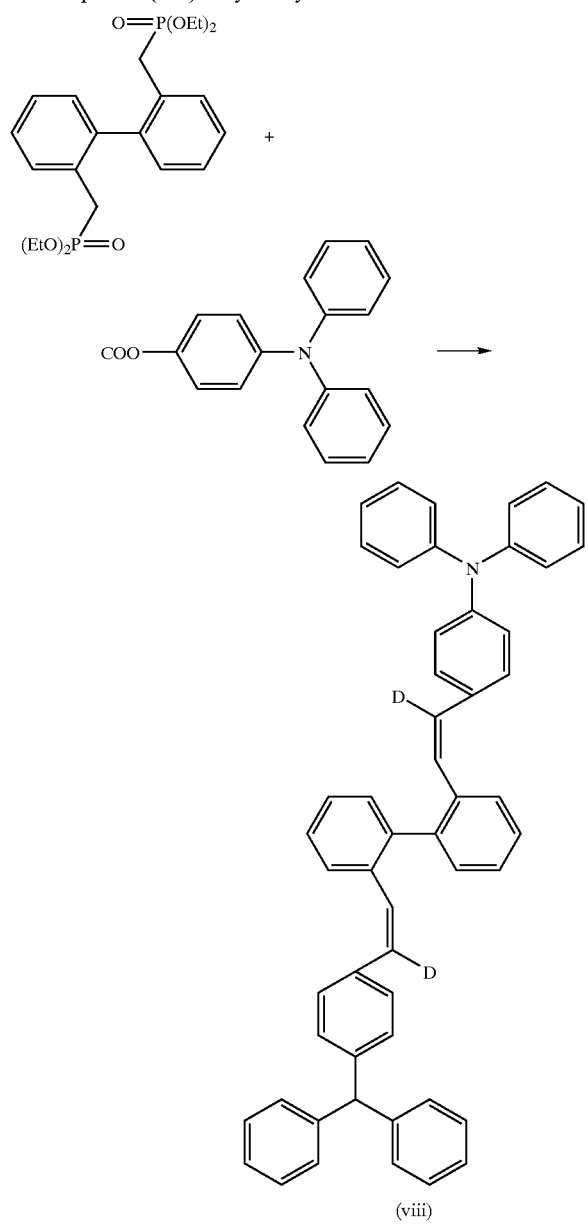

More particularly, compound (viii) was synthesized using the Wittig-Homer reaction as described in W. S. Wadsworth, Jr., W. D. Emmons, *J Am. Chem. Soc.* vol. 83, 1733 (1961). A round flask was charged with a phosphonate carbanion (1.61 g, 3.52 mmol), a triarylamine (2.028 g, 7.39 mmol) and potassium tert-butoxide (KOtBu) (1.24 g, 11.09 mmol) and degassed. To that mixture, 50 mL of dry toluene was added and stirred at room temperature for five minutes. Then the yellow solution was heated to reflux (~120° C.) for seven hours. Then the solution was stored overnight followed by the addition of 300 mL of methanol to yield the precipitate. Water was added to make the suspension a solution and the solution extracted with five 100 mL washes of Dichloromethane ($CHCl_2$). The final product was purified using 2.23 g of haxane to hexane/$CHCl_2$ after TLC analysis showed 2 spots. The result was a yellow solid.

As discussed above, another aspect of the present invention is to provide OLEDs using the compounds previously described. These devices have shown improved performance compared to devices using the conventional host-dopant system.

An OLED is made using the general procedure for OLED fabrication described above. The device has an ITO electrode on a NPD hole transport layer. The electron transport layer is made of $AlQ_3$ and the second electrode is made of magnesium. The emissive layer in this device has a host material consisting of 3,5-bis-pyrene doped with 1% Compound (ii). This blue emitting device shows improved device lifetime in comparison to a similar OLED with the only difference being that the emissive layer was 3,5-bis-pyrene doped with 1% blue Idemitsu dopant.

Another OLED using a compound of the present invention can be made. The emissive layer in this device has a host material consisting of bis-earbazolyl-phenyl doped with 1% Compound (iii). This green emitting device also shows good device time.

The foregoing examples are illustrative only and are not to be deemed limiting of the invention, which is defined by the following claims and is understood to include such obvious variations and modifications as would be obvious to those of ordinary skill in the art.

What is claimed is:
1. A compound as follows:
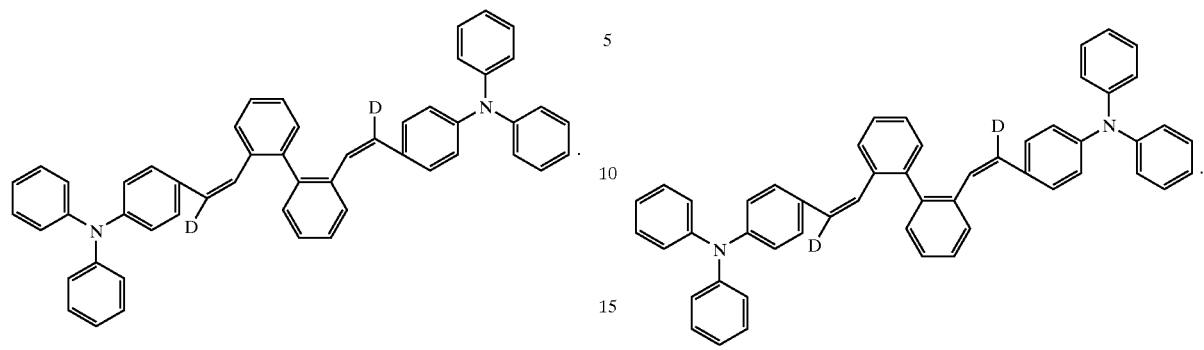
2. An organic light emitting device comprising at least a cathode, an anode and an emissive layer interposed between said cathode and said anode, said emissive layer comprising at least one emissive compound including a compound as follows:
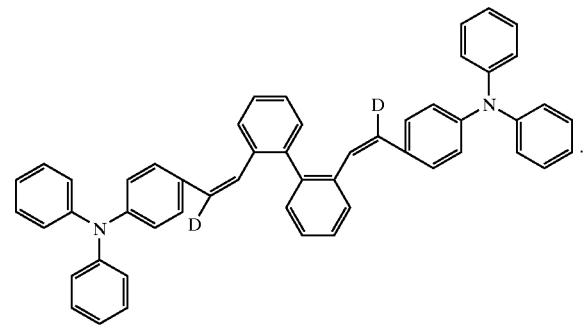
* * * * *

UNITED STATES PATENT AND TRADEMARK OFFICE
CERTIFICATE OF CORRECTION

PATENT NO. : 6,830,834 B2
DATED : December 14, 2004
INVENTOR(S) : Xiao-Chang Charles Li et al.

It is certified that error appears in the above-identified patent and that said Letters Patent is hereby corrected as shown below:

Column 2,
Line 62, "most" should read -- host --.

Column 3,
Line 1, "present" should read -- the present --;
Line 12, "alkyly" should read -- alkyl --;
Line 25, "$H_o\text{-}(L\text{-}G)$," should read -- $H_o\text{-}(L\text{-}G)\text{--}$ --; and
Line 57, "$H_o\text{-}(L\text{-}Q)_n$." should read -- $H_o\text{-}(L\text{-}G)_n$. --.

Column 4,
Line 10, "polycyciic" and should read -- polycyclic --; and
Line 56, "alkyly" should read -- alkyl --;

Column 5,
Line 37, "a" should be deleted.

Column 12,
Line 20, "Wittig-Homer" and should read -- Wittig-Horner --; and
Line 34, "haxane" should read -- hexane --.

Signed and Sealed this

Seventh Day of June, 2005

JON W. DUDAS
*Director of the United States Patent and Trademark Office*